United States Patent [19]

Irikura et al.

[11] Patent Number: 4,654,349
[45] Date of Patent: Mar. 31, 1987

[54] ANTI-ALLERGIC METHODS USING PYRAZOLO(1,5-1)PYRIDINES

[75] Inventors: Tsutomu Irikura, Tokyo; Keigo Nishino, Oomiya; Yoshio Nagatsu, Koga, all of Japan

[73] Assignee: Kyorin Pharmaceutical Co., Ltd., Tokyo, Japan

[21] Appl. No.: 586,945

[22] Filed: Mar. 7, 1984

[30] Foreign Application Priority Data

Mar. 14, 1983 [JP] Japan ................... 58-41957

[51] Int. Cl.$^4$ ............... A61K 31/44; C07D 471/04; C07D 213/89
[52] U.S. Cl. ............................ 514/300; 546/121; 546/311
[58] Field of Search ................. 546/121; 514/300

[56] References Cited

PUBLICATIONS

Seigo Suzue, Masaaki Hirobe, and Toshikiko Okamota, Chem. Pharm. Bull., 21, 2146–2160 (1973).
Robert Morrison and Robert Boyd, "Organic Chemistry", 2nd Ed., Allyn & Bacon Inc., Boston (1966).

Primary Examiner—Henry R. Jiles
Assistant Examiner—Dale A. Bjorkman
Attorney, Agent, or Firm—Armstrong, Nikaido, Marmelstein & Kubovcik

[57] ABSTRACT

The present invention concerns the pyrazolo[1,5-a]pyridine derivatives which are antiallergic agents, referred to as SRS-A release inhibitors, and useful for treatmetn of allergic diseases.

1 Claim, No Drawings

ANTI-ALLERGIC METHODS USING PYRAZOLO(1,5-a)PYRIDINES

DETAILED DESCRIPTION OF THE INVENTION

The present invention is concerned with certain novel pyrazolo[1,5-a]pyridine derivatives which are useful for treatment of allergic diseases, and with compositions containing them.

It is known that chemical mediators are released from certain cells such as mast cells in response to antigen-antibody reaction and induce allergic disorders. The mediators, histamine and SRS-A (slow reacting substance of anaphlaxis), involved in immediate allergic reaction are of importance to medicinal chemists and the SRS-A is particulary noted in allergic asthma.

Accordingly, most major companies have attempted to develop allergic mediator release inhibitors or antagonists against the mediators for treatment of allergic diseases.

Consequently, antihistaminics such as diphenhydramine and chlorpheniramine, and mediator release inhibitors such as disodium cromoglycate are on the market. But antihistaminics have not been proved to be effective in bronchial asthma and disodium cromoglycate must be insufflated as a powder owing to its orally inactive property. Thus no agent satisfying clinical requirement is clearly visible at this time.

It is very important therefore to develop an orally active and more potent drug, referred to as antagonists of SRS-A and SRS-A release inhibitors.

As a result of the investigation, the present inventors, have now unexpectedly found that new derivatives of pyrazolo[1,5-a]pyridine possess a potent antiallergic activity, especially potent inhibitory activity on SRS-A release.

Thus, the present compounds constitute valuable agents which are used in human and veterinary medicine for the treatment of systemic or localized allergic diseases such as bronchial asthma, allergic rhinitis, urticaria and so on.

According to the present invention, therefore, there are provided novel pyrazolo[1,5-a]pyridine derivatives of the formula [I],

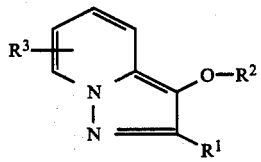

(in which $R^1$ is a hydrogen, straight or branched alkyl radical having 1 to 4 carbon atoms or p-fluorophenyl radical, $R^2$ is a hydrogen, straight or branched acyl radical having 1 to 5 carbon atoms, p-fluorobenzoyl, ethoxycarbonyl, ethoxycarbonylmethyl or carboxymethyl radical and $R^3$ is a hydrogen, methyl or ethyl radical), other than a compound of the formula [I], in which $R^1$ is a methyl radical, $R^2$ is a hydrogen or acetyl radical and $R^3$ is a hydrogen, a compound of the formula [I], in which $R^1$ is an ethyl radical, $R^2$ is a hydrogen or propionyl radical and $R^3$ is a hydrogen, a compound of the formula [I], in which $R^1$ is a n-propyl radical, $R^2$ is a hydrogen or n-butyryl radical and $R^3$ is a hydrogen, a compound of the formula [I], in which $R^1$, $R^2$ and $R^3$ are each a hydrogen and a compound of the formula [I], in which $R^1$ and $R^3$ are each a hydrogen and $R^2$ is a acetyl radical.

The compounds are used intact or in pharmaceutical compositions, which additionally comprise an inert physiologically acceptable carrier. For oral or parenteral administration, suitable forms of pharmaceutical composition are, for example, compressed tablets, capsules, liquores, injections, inhalations, ointments, suppositories and so on.

The present invention also comprises a process for the preparation of the present compounds.

The compound of the formula [I], in which $R^2$ is a $-COR^1$ radical, can be prepared by treating the compound of the formula [II] with an acid anhydride of the formula [III] or acid halide of the formula [IV],

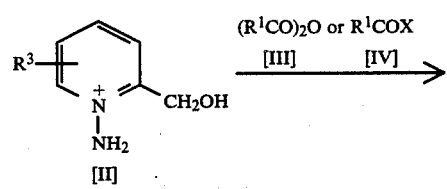

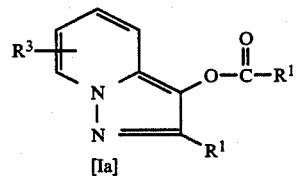

(Wherein $R^1$ and $R^3$ have the above-stated meanings and X is a halogen)

When $R^1$ and $R^2$ in the formula [I] are a hydrogen, the compound has the formula [If],

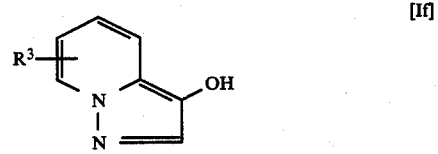

in which $R^3$ is a methyl or ethyl radical, and can be prepared by treating the compound of the formula [II] with orthoformic ester at the presence of sodium or potassium acetate in a suitable solvent such as acetic acid.

The compound of the formula [Ia] obtained hereinbefore can be hydrolyzed to the corresponding 3-hydroxy derivative of the formula [Ib],

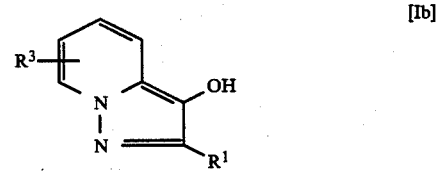

in which $R^1$ and $R^3$ have the above-stated meanings, by the usual method.

The compound of the formula [Ib] can be converted, if necessary, to the compound of the formula [I], in which $R^2$ is an acyl group, by treating with an acid anhydride or acid halide by the usual way. In addition, the compound of the formula [Ib], can be derived to the compound of the formula [I] in which $R^2$ is ethoxycarbonylmethyl radical, by treating with halo acetic ester such as chloro or bromo acetic ethyl in the presence of an alkaline medium such as sodium hydroxide, potassium hydroxide, sodium methoxide and so on in a suitable solvent such as water, methanol, ethanol and the mixture of them.

Further, the ester can be saponified to the corresponding acid of the formula [I], in which $R^2$ is carboxymethyl radical, by the usual manner.

The following examples are illustrative of the products of the present invention, but are not to be construed as limiting.

EXAMPLE 1

6-Ethyl-3-hydroxypyrazolo[1,5-a]pyridine

A mixture of 3.8 g of 1-amino-5-ethyl-2-hydroxy methylpyridinium chloride, 2.5 g of sodium acetate, 25 ml of acetic acid and 8.9 g of ethyl orthoformate was refluxed for 4 hours in an oil bath at 140° C. After evaporated under vacuum, to the residue was added water. The mixture was brought to pH 11 by the addition of potassium carbonate and extracted with ethyl acetate. Ethyl acetate extract was then dried over anhydrous sodium sulfate, decolorized with charcoal and concentrated to dryness. After purification of the oily residue by silica gel column chromatography, eluted with chloroform, the light brown viscous oil that had a yellowish green fluorescence by irradiating of the long wave ultraviolet rays (3650 Å) was obtained. By recrystallization from chloroform-methanol, 1.36 g of the desired product, pale yellow needles, were obtained. Yield: 42.0%, mp 78°-79° C. The result of elemental analysis was illustrated in Table 3.

EXAMPLE 2

6-Ethyl-3-isobutyryloxy-2-isopropylpyrazolo[1,5-a]pyridine

To 6.0 g of 1-amino-5-ethyl-2-hydroxymethylpyridinium chloride were added 25.3 g of isobutyric anhydride and 5 ml of pyridine. The mixture was refluxed for 7 hours in an oil bath at 140° C. After a portion of methanol was added to decompose the excess isobutyric anhydride, the reaction mixture was concentrated by evaporator at 100° C. To the residue was added water and potassium carbonate, and the resulting alkaline mixture was extracted with ethyl acetate. The ethyl acetate extrat was dried over anhydrous sodium sulfate, decolorized with charcoal and concentrated to a brown oil. The oil was purified by silca gel column chromatography, eluted with chloroform, to obtain 3.90 g of the desired product, a pale yellow oil, that had a violet fluorescence by irradiation of the long wave ultraviolet rays (3650 Å). Yield: 44.4%.

EXAMPLE 3

6-Ethyl-3-hydroxy-2-isopropylpyraxolo[1,5-a]pyridine

To 3.90 g of the compound prepared in Example 2 were added 40 ml of 10% hydrochloric acid. The mixture was heated for 2 hours in a water bath at 100° C. After the reaction mixture was made to be alkaline condition (pH 11) with concd. aqueous ammonia (28%), the resulting precipitates were collected by filtration, and then disolved in warm ethyl acetate. The solution was dried over anhydrous sodium sulfate, declolorized with chacoal and condensed to a small volume. By recrystallization from a small of ethyl acetate, 2.32 g of the desired product, pale yellow needles, were obtained. Yield: 81.8%, mp 106°-107° C.

EXAMPLE 4

6-Ethyl-3-propionyloxypyrazolo[1,5-a]pridine

To 600 mg of the compound prepared in Example 1 were added 5.1 g of propionic anhydride. The mixture was heated for 4 hours in a water bath at 90° C. After concentrating the reaction mixture, it was purified by using the procedure described in Example 2 to give 607 mg of the desired product, a pale yellow oil, that had a blue fluorescence by irradiating of the long wave ultraviolet rays (3650 Å). Yield: 75.1%.

EXAMPLE 5

3-Ethoxycarbonyloxy-6-ethyl-2-isopropylpyrazolo[1,5-a]pyridine

The compound (1.02 g) prepared in Example 3 which was dissolved in 50 ml of dichloromethane was added to 1.09 g of ethyl chloroformate. To the reaction mixture was added dropwise 1.0 g of triethylamine. The mixture was refluxed for 1 hour in a water bath at 60° C., and then cooled to room temperature. The mixture was diluted with 50 ml of water and extracted with dichloromethane. The dichloromethane extract was dried over anhydrous sodium sulfate, concentrated to dryness and purified by silica gel column chromatography, eluted with chloroform to yield 1.02 g of the desired product, a pale yellow oil, that had a violet fluorescence by irradiating of the long wave ultraviolet rays (3650 Å). Yield: 73.9%.

EXAMPLE 6

3-Ethoxycarbonylmethyloxy-6-ethyl-2-isopropyl-pyrazolo[1,5-a]pyridine

To a solution of 1.25 g of the compound prepared in Example 3 in 20 ml of ethanol was added a solution of 400 mg of potassium hydroxide in 20 ml of ethanol, and the mixture was stirred for about 10 minutes at room temprature. Then the reaction mixture was refluxed for 1 hour in a water bath at 90° C. after adding of 2.0 g of ethyl bromoacetate. After removrval of the white precipitate by filtration, the filtrate was concentrated with evaporator. The residue was extracted with hexane. The hexane extract was decolorized with chacoal, concentrated and purified by silica gel column chromatography, eluted with chloroform to yield 1.13 g of the desired product, a pale yellow oil, that had a blue-green fluorscence by irradiating of the long wave ultraviolet rays (3650 Å). Yield: 63.8%.

EXAMPLE 7

3-Carboxymethyloxy-6-ethyl-2-isopropylpyrazolo[1,5-a]-pyridine

To 500 mg of the compound prepared in Example 6 were added 20 ml of 2N sodium hydroxide solution, and the mixture was heated for 1 hour in a water bath at 90° C. The reaction mixture was neutrallized with 2N hydrochloric acid to be acidic condition (pH 3) under cooling in an ice bath. The resulting precipitates were collected by filtration and recrystallized from a mixture of benzene and hexane to give 374 mg (83.9%) of the desired product as colorless powder, mp 118°-119° C.

EXAMPLE 8

3-p-Fluorobenzoyloxy-2-p-fluorophenylpyrazolo[1,5-a]pyridine

To a solution of 7.0 g of p-fluorobenzoic acid in 20 ml of benzene dried over sodium, were added 25 g of thionylchloride, and the mixture was refluxed for 4 hours. After concentrating of the reaction mixture at 60° C., the residue was dissolved in 20 ml of chloroform. The chloroform solution was added to the mixture of 2.7 g of 1-amino-2-hydroxymethylpyridinium chloride (R³ is a hydrogen in the formula [III]) and 4.6 g of potassium carbonate in 30 ml of water, then the mixture was stirred for 6 hours at room temperature. After filtration of the resulting precipitate, the chloroform layer was separated, concentrated and purified by silica gel column chromatography, eluted with chloroform. The desired product (994 mg), colorless needles, was obtained by recrystallization from methanol. Yield: 17.0%, mp 221° C.

EXAMPLE 9

2-p-Fluorophenyl-3-hydroxypyrazolo[1,5-a]pyridine

To a solution of 700 mg of the compound prepared in Example 8 in 20 ml of ethanol were added 20 ml of 1N sodium hydroxide solution and the mixture was refluxed for 30 minutes in a water bath at 90° C. The reaction mixture was condensed, neutrallized with 1.7 ml of concd. hydrochloric acid, and then diluted with 50 ml of water. The precipitates were collected by filtration and recrystallized from benzene to give 223 mg (48.8%) of the title compound as colorless needles, mp 178°–179° C.

The compounds of Nos. 2, 3, and 5, the compounds of Nos. 8 to 12 and 20 and the compounds of Nos. 13, 14 and 16 were prepared by using the procedure described in Example 3, Example 4 and Example 2, respectively. Those yield, melting point, recrystallization solvent and the result of elemental analysis were illustrated in Table 3.

In the present invention the starting material, the compound of the formula [II], could be prepared from the corresponding derivatives of pyridine-2-methanol.

REFERENCE EXAMPLE 1

1-Amino-5-ethyl-2-hydroxymethyl pyridinium chloride

To a mixture of 45.2 g of hydroxylamine-O-sulfate and 150 ml of water was slowly added a mixture of 26.1 g of potassium hydroxide and 30 ml of water over a period of about 15 minutes under stirring and cooling at 0°–5° C. by an ice-salt bath. A solution of 33.2 g of 5-ethyl-2-pyridine-methanol and 50 ml of water was added to the reaction mixture. After warming and stirring for 2 hours at 70° C., the reaction mixture was made to pH 10 with 27.6 g of potassium carbonate under cooling in an ice bath, and extracted with chloroform. The chloroform layer was concentrated, 19.5 g of 5-ethyl-2-pyridinemethanol were recovered. On the other hand, the alkaline aqueous solution was made to pH 1 with 20 ml of concd. hydrochloric acid, and then evaporated to dryness at 100° C. The residue was extracted with warm ethanol, and the ethanol solution was concentrated to dryness. The residue was recrystallized from a small volume of ethanol to give 14.0 g (30.7%) of the desired product as pale yellow prisms, mp 140°–141° C. Analysis of this compound gave: C, 50.81%; H, 7.05%; N, 14.68%. Calculated for $C_8H_{13}N_2OCl$: C, 50.93%; H, 6.95%; N, 14.85%.

REFERENCE EXAMPLE 2

1-Amino-2-hydroxymethyl-6-methylpyridinium chloride

According to the procedure described in Reference example 1, 3.5 g of the title compound (R³ is 6-methyl radical in the formula [II]) were obtained from 20.8 g of 6-methyl-2-pyridinemethanol. Yield: 11.8%, mp 163°–164° C. Analysis of this compound gave: C, 48.17%; H, 6.48%; N, 16.09%. Calculated for $C_7H_{11}N_2OCl$: C, 48.15%; H, 6.35%; N, 16.09%.

EXPERIMENT 1

Inhibitory effect on SRS-A release

The inhibitory effect of the compounds of this invention on SRS-A release was determined according to the method of Orange and Moors [J. Immunol., 116, 392 (1976)]. SRS-A released from chopped lung fragments of sensitized guinea pigs upon antigen challenge was bioassayed on isolate guinea pig ileum according to the method of Brocklehurst [J. Physiol., 151, 416 (1960)]. Test compounds were preincubated with lung fragments prior to antigen challenge.

As shown in Table 1, the compounds of this invention inhibited the immunological release of SRS-A at considerably low concentrations. A reference drug phenidone was 2 to 10 times less active than the compounds of this invention.

TABLE 1

| Compd. No. | Inhibitory activity on SRS-A release $IC_{50}$ (× $10^{-6}$ g/ml)* |
|---|---|
| 1 | 0.55 |
| 2 | 1.4 |
| 3 | 0.63 |
| 4 | 3.5 |
| 5 | 1.8 |
| 6 | 2.4 |
| 7 | 1.0 |
| 8 | 1.7 |
| 9 | 1.0 |
| 10 | 1.7 |
| 11 | 0.70 |
| 12 | 0.52 |
| 13 | 0.88 |
| 14 | 0.53 |
| 15 | 1.2 |
| 16 | 1.9 |
| 17 | 1.5 |
| 20 | 2.4 |
| phenidone** | 6.3 |

*concentration of test compound required to produce a 50% inhibition of SRS-A release.
**1-phenyl-3-pyrazolidone, the chemical structure is as follows.

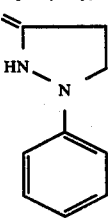

EXPERIMENT 2

Effect on metabolism of arachidonic acid

The effect of the compounds of this invention on the metabolism of exogenous arachidonic acid-1-$^{14}$C was determined essentially according to the method of Harvey and Osborne [J. Pharmacol. Methods 9, 147 (1983)] using guinea pig peritoneal neutrophils stimulated with calcium ionophore A23187. With this procedure, 5-hydroxyeicosatetraenoic acid (a 5-lipoxygenase product) and 12-hydroxy-5,8,10-heptadecatrienoic acid (a cyclooxygenase product) were produced by neutrophils as major metabolites, allowing simultaneous evaluation of the drug effect on both pathways of arachidonic acid metabolism.

As shown in Table 2, the compounds of this invention inhibited the synthesis of 5-lipoxygenase product without affecting cyclooxygenase pathway. These compounds were several times as potent inhibitors of 5-lipoxygenase as phenidone. SRS-A is well-known to be synthesized from arachidonic acid via 5-lipoxygenase pathway. Therefore, it is concluded that the compounds of this invention inhibit SRS-A release by acting as 5-lipoxygenase inhibitor.

TABLE 2

| | | Effect on arachidonic acid metabolism | |
|---|---|---|---|
| | Concentration | Inhibition percent | |
| Compd. No. | (μM) | 5-Lipoxygenase | Cyclooxygenase |
| 5 | 0.1 | 20.3 | 0 |
| | 1.0 | 86.6 | 0 |
| 7 | 0.1 | 62.0 | 0 |
| | 0.3 | 84.0 | 0 |
| 9 | 0.1 | 35.1 | 0 |
| | 0.3 | 61.7 | 0 |
| 10 | 0.1 | 20.6 | 0 |
| | 0.3 | 80.2 | 0 |
| 12 | 0.1 | 53.2 | 0 |
| 16 | 0.1 | 16.9 | 0 |
| | 0.3 | 82.1 | 0 |
| 20 | 1.0 | 83.7 | 0 |
| phenidone | 0.3 | 22.0 | 0 |
| | 1.0 | 60.0 | 0 |
| | 3.0 | 89.0 | 0 |
| | 30.0 | 95.5 | 58.2 |

TABLE 3

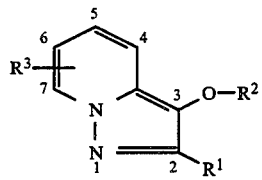

[I]

| Compd. No. | $R^1$ | $R^2$ | $R^3$ | Yield (%) | M.p. (°C.) and b.p. (°C./mmHg) | Recryst. solvent[b] | Formula | Calcd. (%) C | H | N | Found (%) C | H | N |
|---|---|---|---|---|---|---|---|---|---|---|---|---|---|
| 1 | H | H | 6-$C_2H_5$ | 42.0 | 78–79 | CH | $C_9H_{10}N_2O$ | 66.65 | 6.21 | 17.27 | 66.63 | 6.18 | 17.11 |
| 2 | $CH(CH_3)_2$ | H | H | 25.6 | 121–122 | AH | $C_{10}H_{12}N_2O$ | 68.16 | 6.86 | 15.90 | 68.16 | 6.88 | 15.74 |
| 3 | $CH(CH_3)_2$ | H | 7-$CH_3$ | 67.6 | 143–144 | AH | $C_{11}H_{14}N_2O$ | 69.45 | 7.42 | 14.72 | 69.50 | 7.52 | 14.67 |
| 4 | $CH(CH_3)_2$ | H | 6-$C_2H_5$ | 81.1 | 106–107 | A | $C_{12}H_{16}N_2O$ | 70.56 | 7.90 | 13.71 | 70.40 | 7.91 | 13.59 |
| 5 | $CH_2CH(CH_3)_2$ | H | H | 89.9 | oil 122–123[a] | E | $C_{17}H_{17}N_5O_8$ | 48.69 | 4.09 | 16.70 | 48.57 | 4.07 | 16.69 |
| 6 | –⟨⟩–F | H | H | 48.8 | 178–179 | B | $C_{13}H_9N_5OF$ | 68.42 | 3.97 | 12.27 | 68.31 | 3.81 | 12.23 |
| 7 | H | $COC_2H_5$ | 6-$C_2H_5$ | 75.1 | oil 103[a] | E | $C_{18}H_{17}N_5O_9$ | 48.33 | 3.83 | 15.65 | 48.07 | 3.83 | 15.66 |
| 8 | $CH_3$ | $COCH(CH_3)_2$ | H | 82.9 | bp 124–126/ 2 mmHg 121–122[a] | M | $C_{18}H_{17}N_5O_9$ | 48.33 | 3.83 | 15.65 | 48.28 | 3.77 | 15.64 |
| 9 | $C_2H_5$ | $COCH_3$ | H | 73.2 | 36–365 | | $C_{11}H_{12}N_2O_2$ | 64.69 | 5.92 | 13.72 | 64.67 | 5.85 | 13.68 |
| 10 | $CH_2CH_2CH_3$ | $COCH_3$ | H | 35.5 | oil 123–124[a] | E | $C_{18}H_{17}N_5O_9$ | 48.33 | 3.83 | 15.65 | 48.32 | 3.75 | 15.64 |
| 11 | $CH(CH_3)_2$ | $COCH_3$ | H | 74.9 | oil 131–132[a] | E | $C_{18}H_{17}N_5O_9$ | 48.33 | 3.83 | 15.65 | 48.34 | 3.79 | 15.66 |
| 12 | $CH(CH_3)_2$ | $COCH_2CH_3$ | H | 89.1 | oil 108–109[a] | E | $C_{19}H_{19}N_5O_9$ | 49.46 | 4.15 | 15.18 | 49.46 | 4.10 | 15.08 |
| 13 | $CH(CH_3)_2$ | $COCH(CH_3)_2$ | H | 34.8 | bp 131–134/ 2 mmHg 33–34 | | $C_{14}H_{18}N_2O_2$ | 68.27 | 7.37 | 11.37 | 68.35 | 7.54 | 11.48 |
| 14 | $CH(CH_3)_2$ | $COCH(CH_3)_2$ | 7-$CH_3$ | 36.8 | oil 101–102[a] | E | $C_{21}H_{23}N_5O_9$ | 51.53 | 4.74 | 14.31 | 51.47 | 4.74 | 14.30 |
| 15 | $CH(CH_3)_2$ | $COCH(CH_3)_2$ | 6-$C_2H_5$ | 44.4 | oil 97–100[a] | E | $C_{22}H_{25}N_5O_9$ | 52.48 | 5.01 | 13.91 | 52.41 | 5.04 | 13.88 |
| 16 | $CH_2CH(CH_3)_2$ | $COCH_2CH(CH_3)_2$ | H | 51.2 | oil | | $C_{16}H_{22}N_2O_2$ | 70.04 | 8.08 | 10.21 | 70.02 | 8.17 | 10.18 |
| 17 | $CH(CH_3)_2$ | $COOC_2H_5$ | 6-$C_2H_5$ | 73.9 | oil 109–110[a] | E | $C_{21}H_{23}N_5O_{10}$ | 49.90 | 4.59 | 13.86 | 49.90 | 4.55 | 13.81 |
| 18 | $CH(CH_3)_2$ | $CH_2COOC_2H_5$ | 6-$C_2H_5$ | 63.8 | 109–111[a] | E | $C_{22}H_{25}N_5O_{10}$ | 50.87 | 4.85 | 13.48 | 50.74 | 4.87 | 13.43 |
| 19 | $CH(CH_3)_2$ | $CH_2COOH$ | 6-$C_2H_5$ | 83.9 | 118–119 | BH | $C_{14}H_{18}N_2O_3$ | 64.11 | 6.92 | 10.68 | 64.59 | 6.99 | 10.47 |
| 20 | –⟨⟩–F | $COCH_3$ | H | 64.8 | 140–141 | E | $C_{15}H_{11}N_2O_2F$ | 66.66 | 4.10 | 10.37 | 66.68 | 3.92 | 10.30 |

TABLE 3-continued

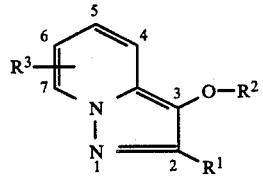

| Compd. No. | R¹ | R² | R³ | Yield (%) | M.p. (°C.) and b.p. (°C./mmHg) | Recryst. solvent[b] | Formula | Analysis Calcd. (%) C H N | Analysis Found (%) C H N |
|---|---|---|---|---|---|---|---|---|---|
| 21 | —⟨⟩—F | CO—⟨⟩—F | H | 17.0 | 221 | M | $C_{20}H_{12}N_2O_2F_2$ | 68.57 3.45 8.00 | 68.45 3.27 8.01 |

[a] picrate
[b] A: ethyl acetate, AH: ethyl acetate-hexane, B: benzene, BH: benzene-hexane, CH: chloroform-hexane, E: ethanol, M: methanol.

What is claimed is:

1. A method of treatment for allergic diseases comprising administering to a patient requiring such treatment an anti-allergic effective amount of a pyrazolo[1,5-a]pyridine derivative of the formula [I],

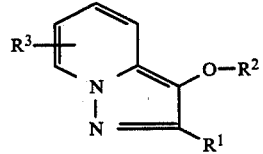

(in which R¹ is a hydrogen, straight or branched alkyl radical having 1 to 4 carbon atoms or p-fluorophenyl radical, R² is a hydrogen, straight or branched alkyl carbonyl radical having 1 to 5 carbon atoms, p-fluorobenzoyl, ethoxycarbonyl, ethoxycarbonylmethyl or carboxymethyl radical and R³ is a hydrogen, methyl or ethyl radical), other than a compound of the formula [I], in which R¹ is a methyl radical, R² is a hydrogen or acetyl radical and R³ is a hydrogen, a compound of the formula [I], in which R¹ is an ethyl radical, R² is a hydrogen or propionyl radical and R³ is a hydrogen, a compound of the formula [I], in which R¹ is a n-propyl radical, R² is a hydrogen or n-butyryl radical and R³ is a hydrogen, a compound of the formula [I], in which R¹, R² and R³ are each a hydrogen and a compound of the formula [I], in which R¹ and R³ are each a hydrogen and R² is a acetyl radical.

* * * * *

UNITED STATES PATENT AND TRADEMARK OFFICE
CERTIFICATE OF CORRECTION

PATENT NO. : 4,654,349
DATED : March 31, 1987
INVENTOR(S) : TSUTOMU IRIKURA ET AL It is certified that error appears in the above-identified patent and that said Letters Patent is hereby corrected as shown below:

On the cover page, Item 54, change "(1,5-1)" to

--- [1,5-a] ---.

Signed and Sealed this

First Day of September, 1987

Attest:

DONALD J. QUIGG

Attesting Officer

Commissioner of Patents and Trademarks